US00PP37762P2

(12) United States Plant Patent
Clarkson

(10) Patent No.: US PP37,762 P2
(45) Date of Patent: Oct. 13, 2026

(54) ***FRAGARIA* PLANT NAMED 'EW195'**

(50) Latin Name: ***Fragaria* x *ananassa***
Varietal Denomination: EW195

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 19/533,152

(22) Filed: Feb. 7, 2026

(30) Foreign Application Priority Data

Jan. 6, 2026 (QZ) ..... PBR 2026/0015

(51) Int. Cl.
*A01H 5/08* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

PP37,418 P2 * 5/2026 Clarkson ..... Plt./209

* cited by examiner

*Primary Examiner* — Karen M Redden
(74) *Attorney, Agent, or Firm* — Penny J. Aguirre

(57) ABSTRACT

A new cultivar of *Fragaria* plant named 'EW195' that is characterized by its fruit that are highly sweet with low acidity, its high fruit yields that stays consistent throughout the season, its fruit that are conical in shape and highly glossy, highly juicy, and medium red in color, its fruit with even texture across the surface with the achenes level to the fruit surface, its, and its fruit with firm skin and flesh, resulting in a very good post-harvest shelf life.

3 Drawing Sheets

Botanical classification: *Fragaria* x *ananassa.*
Variety denomination: 'EW195'.

CROSS-REFERENCE TO RELATED APPLICATIONS

This application claims priority to European Community Plant Variety Office (CPVO) Plant Breeder's Rights Application No. 2026/0015 filed on Jan. 6, 2026, under 35 U.S.C. 119(f), the entire contents of which is incorporated by reference herein. This application is also related to a plant breeders' rights application in The United Kingdom on Jan. 6, 2026, Application No. 10/230. The information for the plant breeders' rights applications was received directly from the Inventor.

BACKGROUND OF THE INVENTION

The present invention relates to a new and distinct cultivar of *Fragaria*, botanically known as *Fragaria* x *ananassa* 'EW195' and will be referred to hereafter by its cultivar name, 'EW195'. 'EW195' is an everbearing strawberry plant primarily adapted to the climate and growing conditions of The United Kingdom and other regions of similar climate and day length for use in the fresh fruit market.

The new cultivar was derived from an ongoing breeding program conducted by the Inventor in Faversham, Kent, United Kingdom. The goal of the breeding program was to develop a new cultivar of *Fragaria* with large fruit having high yields, uniform shape, fruit firmness, pleasant flavor, good eating quality, low acidity, and consistent cropping combined with high disease tolerance. 'EW195' arose from a controlled cross made by the Inventor in 2018 between *Fragaria* cultivars from the Inventor's breeding program, *Fragaria* 'Eves Joy' (U.S. Plant Pat. No. 5,911 P3) as the female parent and *Fragaria* 'Eves Delight 2' (U.S. Plant Pat. No. 32,418) as the male parent. 'EW195' was selected in Faversham, Kent, The United Kingdom as a single unique plant in the Summer of 2019 from amongst the seedlings that resulted in the above cross.

Asexual propagation of the new cultivar was first accomplished by rooting stolons in Faversham, Kent, The United Kingdom in 2019. Asexual propagation by rooting of stolons and tissue culture using meristematic tissue has shown that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'EW195' as a unique cultivar of *Fragaria.*

1. 'EW195' exhibits fruit that are highly sweet with low acidity.
2. 'EW195' exhibits high fruit yields that stays consistent throughout the season.
3. 'EW195' exhibits fruit that are conical in shape and highly glossy, highly juicy, and medium red in color.
4. 'EW195' exhibits fruit with even texture across the surface with the achenes level to the fruit surface.
5. 'EW195' exhibits dense plants that are strong in vigor.
6. 'EW195' exhibits fruit with firm skin and flesh, resulting in a very good post- harvest shelf life.

The female parent of 'EW195' differs from 'EW195' in having slightly larger fruit that are darker red in color and a less vigorous plant habit. The male parent of 'EW195' differs from 'EW195' in having fruit that are smaller in size, orange-red in color, have firmer skin, and less Class I yield overall.

'EW195' can be compared to *Fragaria* cultivars 'PGP182' (U.S. Plant Pat. No. 37,208) and 'CH67' (U.S. Plant Pat. No. 37,418).

'PGP182' is similar to 'EW195' in having high fruit yields throughout the season, fruit with high juiciness, high gloss, and firm skin and flesh with good post-harvest shelf life when tested against bruising and changes to color, and a similar plant habit and vigor. 'PGP182' differs from 'EW195' in having less percentage of fruit deemed Class I quality, fruit that is conical-reniform in shape, slightly more aromatic, achenes that are present more deeply below the surface, deeper red skin coloration, and lower sugar and acidity levels, and foliage that is darker green in color. 'CH67' is similar to 'EW195' in having large fruit that is highly sweet, and glossy with a good post-harvest shelf life. 'CH67' differs in producing fruit that is orange-red in color, slightly firmer, more aromatic, and achenes that are presented primarily below the fruit surface.

BRIEF DESCRIPTION OF THE DRAWINGS

The accompanying color photographs illustrate the overall appearance and distinct characteristics of the new *Fragaria*. The photographs were taken of 3-month-old plants (from rooted cuttings) of 'EW195' as grown on table-tops in coir bags under tunnels with polyethylene covers in Faversham, Kent, United Kingdom.

The photograph in FIG. 1 provides a view of 'EW195' bearing fruit.

Figure 1:
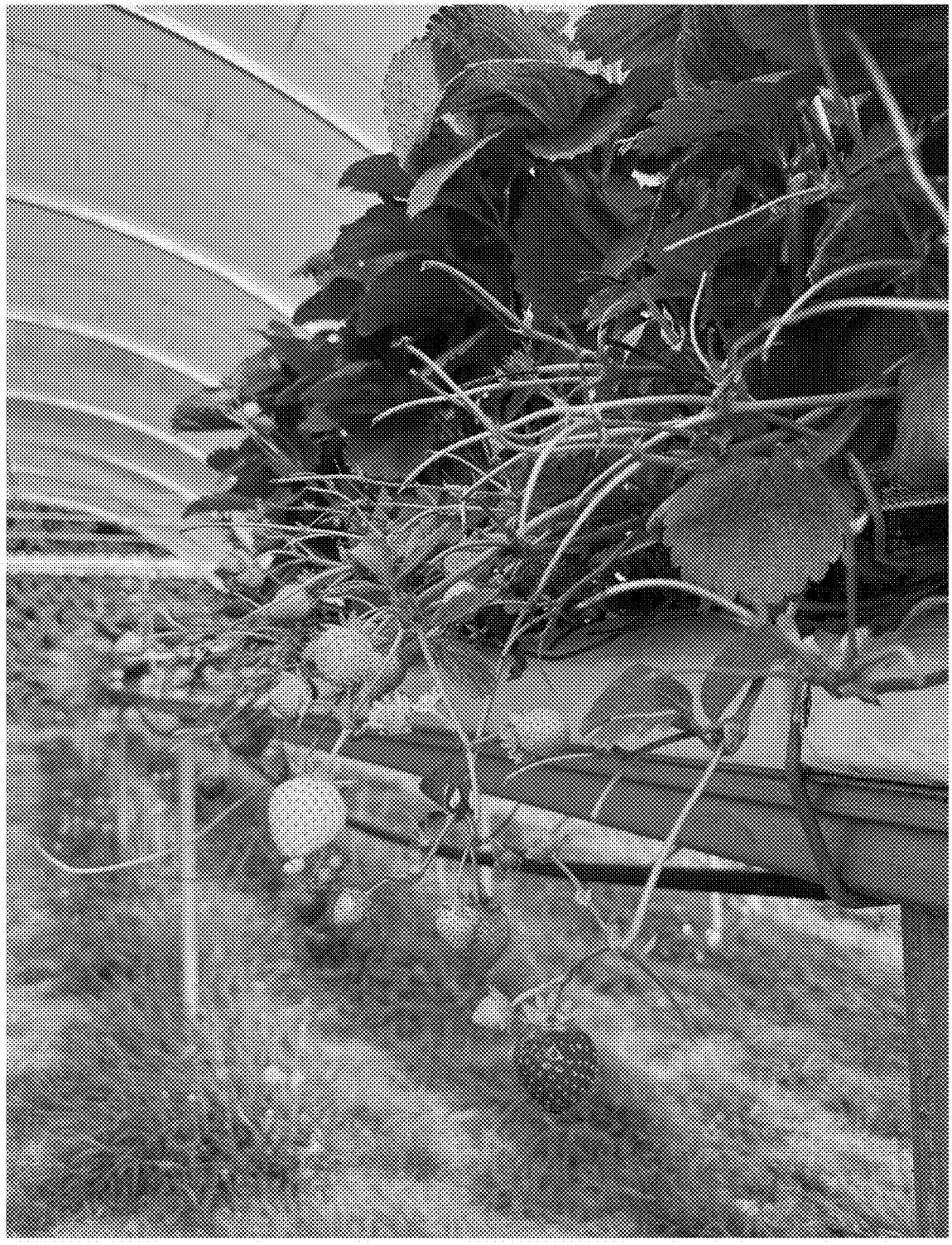
Figure 2:
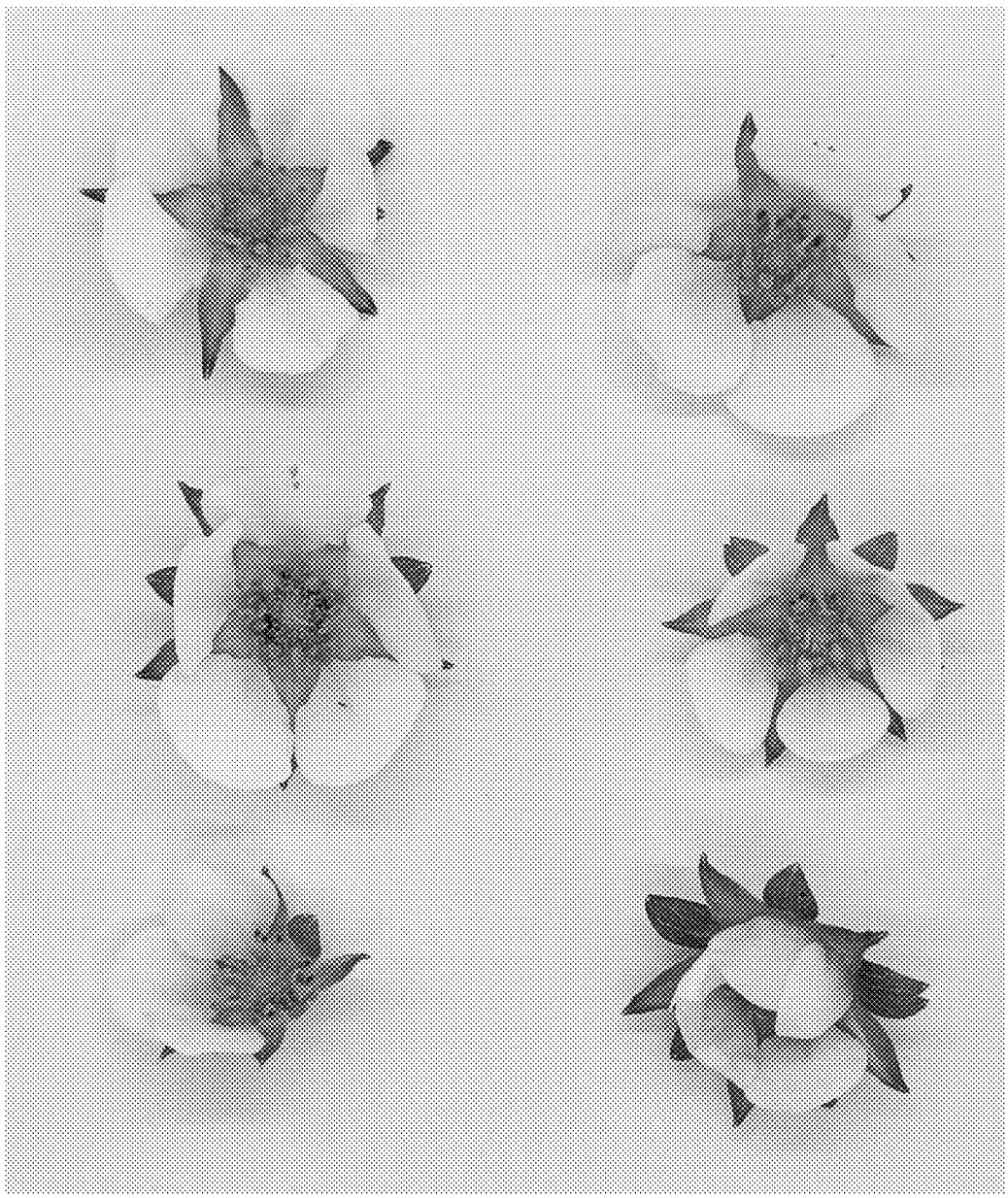

The photograph in FIG. 2 provides a close-up view of the flowers of 'EW195'.

Figure 3:
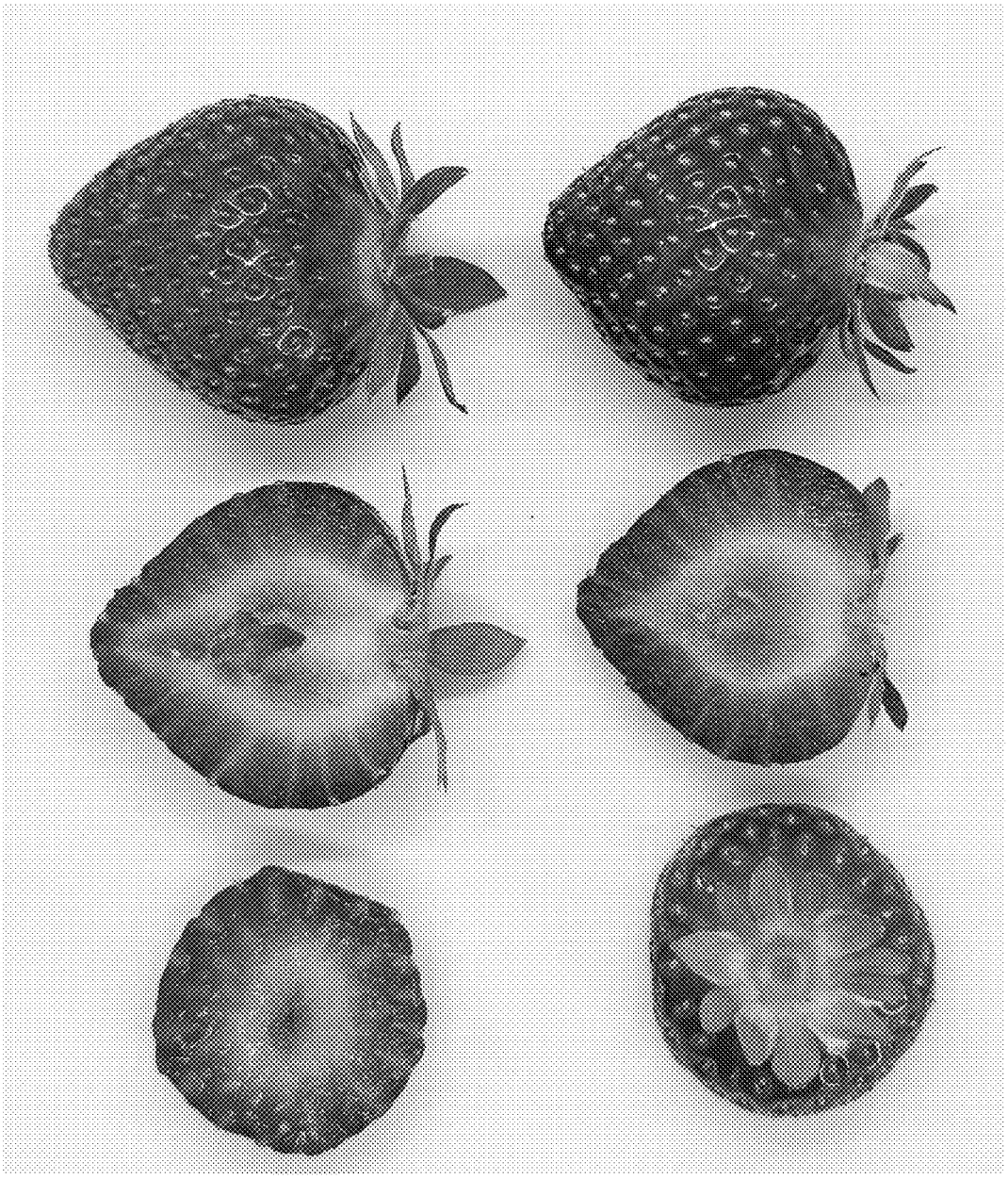

The photograph in FIG. 3 provides a close-up view of the fruit of 'EW195' (whole fruit top, vertical cross section middle, horizontal cross section bottom).

The colors in the photographs are as close as possible with the photographic and printing technology utilized and the color values cited in the detailed botanical description accurately describe the colors of the new *Fragaria*.

BOTANICAL DESCRIPTION OF THE PLANT

The following is a detailed description of 3-month-old plants (from rooted cuttings) of 'EW195' as grown outdoors on tabletops in coir bags, under polyethylene tunnels in Faversham, Kent, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—Starting April and produced throughout the Summer in Faversham, Kent, United Kingdom.
- *Plant type*.—Herbaceous fruit producing perennial.
- *Plant habit*.—Semi-upright with a dense canopy and strong vigor.
- *Height and spread*.—Reaches an average of 44.49 cm in height and 62.27 cm in width as a 3-month-old plant grown in a coir bag (an average height to width ratio of 0.8).
- *Cold hardiness*.—Not tested in areas where temperatures below 32° F. occur.
- *Diseases and pests*.—Tolerant to *Botryotinia cinerea* and slight susceptibility to *Podosphaera leucotricha* (powdery mildew) as observed under conditions in Faversham, Kent, the United Kingdom, no susceptibility or resistance to pests has been observed.
- *Root description*.—Fibrous, NN155D in color.
- *Root development*.—An average of 2 weeks to initiate roots and 5 weeks to produce a young rooted plant from a rooted cutting.
- *Propagation*.—Rooting of stolons and tissue culture.
- *Growth rate*.—Vigorous.
- *Stem description*.—Acaulescent.
- *Stolon description*.—Average of 9 per plant, 4 nodes per stolon, ranging between 18.2 cm to 4.6 cm between nodes, sparsely to moderately pubescent surface, color 144B.

Foliage description:

- *Leaf division*.—Compound, three leaflets.
- *Leaf arrangement*.—Basal.
- *Leaf attachment*.—Petiolate.
- *Leaflet shape*.—Rounded.
- *Leaf size*.—Average of 12.84 cm in length and 22.74 cm in width.
- *Leaflet size*.—Terminal leaflet; average of 11.47 cm in length and 10.01 cm in width, lateral leaflet; average of 11.62 cm in length and 10.06 cm in width.
- *Leaflet margins*.—Serrate to crenate, with an average of 20.6 serrations per leaf.
- *Leaflet base*.—Mostly acute with some obtuse.
- *Leaflet apex*.—Rounded.
- *Leaflet glossiness*.—High gloss.
- *Leaflet aspect*.—Mostly concave with some leaflets straight.
- *Leaflet interveinal blistering*.—Absent.
- *Leaflet venation*.—Pinnate, coloration matches leaflet color.
- *Leaflet surface*.—Both surfaces slightly glossy, upper surface glabrous, lower surface slightly pubescent, main vein slightly pubescent.
- *Leaflet color*.—Upper surface; 146A, lower surface; 147C.
- *Petioles*.—Round in shape, 145B in color, average of 27.97 cm in length and 4.6 mm in width, surface is weakly pubescent.
- *Petiolules*.—Round in shape, 145B in color, average of 1.49 cm in length and 2.8 mm in width, surface weak to moderately pubescent.
- *Stipule*.—Average of 2.79 cm in length and 1.05 cm in width, 145B in color.

Flower description:

- *Inflorescence*.—Truss.
- *Inflorescence size*.—Average of 12.62 cm in length and 20.04 cm in width, including peduncle and pedicel.
- *Flower initiation and expression conditions*.—Temperature dependent.
- *Time of flowering* (50% *of plants at first flower*).—Early season.
- *Flower position relative to foliage*.—Mostly same level or beneath the leaf canopy.

*Flower size.*—2.05 cm in diameter.

*Flower number per truss.*—Average of 5.5 flowers.

*Flower fragrance.*—Weak-typical of species.

*Calyx.*—Average of 3.21 cm in diameter and the same size or larger in relation to the corolla, similar for primary, secondary and tertiary flowers.

*Sepals.*—Average of 10.5 per flower, average of 1.29 cm in length and 5.2 mm in width, acute base, acute apex, color; upper surface 143C, lower surface 143A.

*Sepal position.*—Mostly raised or level in relation to the fruit, some upwards and some outwards in attitude.

*Petals.*—5 to 6, average of 1.08 cm in length and 1.12 cm in width, acute base and rounded apex, mostly touching or overlapping in arrangement with some not touching, entire margins, glabrous upper and lower surfaces, NN155D in color.

*Peduncles.*—Moderately strong, average of 12.22 cm in length and 5.6 mm in width, 144B in color, surface moderately pubescent.

*Pedicels.*—Moderately strong, average of 9.96 cm in length and 4.1 mm in width, 144B in color, surface is moderately pubescent.

*Bracts.*—Observed on majority of the flowering trusses at point of branching from early developmental stage, which progresses into a small single leaflet as the truss matures and the fruit develops, average of 5.15 cm in length and 17.5 mm in width, both surfaces 146A in color.

Reproductive organs:

*Gynoecium.*—Average of 3.9 mm in height and 5.2 mm in width, dome-shaped, apocarpous with multiple simple carpels present with capitate-shaped stigma.

*Androecium.*—Stamens; average of 18.4 per flower, anthers; average of 1.6 mm in length and 0.72 mm in diameter.

Fruit description:

*Shape.*—Conical, similar for primary, secondary and tertiary fruit, apex of the fruit is mostly acute and calyx side of the fruit is mostly rounded.

*Season of harvest.*—May to the end of October in Faversham, Kent, the United Kingdom.

*Time of ripening* (50% *of plants with first ripe fruit*).—Early.

*Type of bearing.*—Everbearing.

*Size.*—Large, average of 4.16 cm in length and 3.74 cm in width.

*Surface.*—Smooth with strong glossiness.

*Calyx position.*—Mixed with some level and some upwards in relation to the fruit, similar for primary, secondary and tertiary fruit.

*Attitude of calyx segments.*—Mixed, some upwards and some outwards.

*Diameter of calyx relative to fruit diameter.*—Same size or larger.

*Glossiness.*—Strong.

*External color* (*skin*).—N43A, color is retained throughout the cropping season.

*Internal color* (*flesh*).—33A, near the core 35A.

*Evenness of color of skin.*—Very even.

*Evenness of color of flesh.*—Paler near center.

*Acidity.*—Low, total titratable acid average of 0.68% over three seasons in trials.

*Sweetness.*—High.

*Soluble solids.*—Average of 10° over three seasons in trials.

*Firmness.*—Skin is very firm (resistant to bruising), flesh is firm.

*Juiciness.*—High.

*Aroma.*—Slight.

*Weight.*—Average of 19.6g per berry and 1530g per plant from late May to end of October over three seasons in trials.

*Number of fruit per plant.*—Average of 78.1 fruits per plant from late May to end of September over three seasons in trials.

*Hollow center.*—Slight on primary, secondary and tertiary fruit, more prominent on primary fruit.

*Shelf life.*—Good, at least 7 days in cold storage.

*Achene color.*—15B.

*Achene position.*—Majority level with the fruit surface.

*Achene number.*—An average of 250 per berry.

*Band without achenes.*—Absent.

*Market use.*—High shipping quality fruit for fresh fruit consumption.

It is claimed:

1. A new and distinct cultivar of *Fragaria* plant named 'EW195' substantially as herein illustrated and described.

* * * * *